(12) United States Patent
Patil et al.

(10) Patent No.: US 9,598,225 B2
(45) Date of Patent: Mar. 21, 2017

(54) CHILD RESISTANT PUMPS

(71) Applicant: MeadWestvaco Corporation, Richmond, VA (US)

(72) Inventors: Bipin Raman Patil, Richmond, VA (US); Douglas B. Dobbs, Chesterfield, VA (US)

(73) Assignee: WestRock MWV, LLC, Norcross, GA (US)

( * ) Notice: Subject to any disclaimer, the term of this patent is extended or adjusted under 35 U.S.C. 154(b) by 0 days.

(21) Appl. No.: 14/440,460

(22) PCT Filed: Nov. 14, 2013

(86) PCT No.: PCT/US2013/069999
§ 371 (c)(1),
(2) Date: May 4, 2015

(87) PCT Pub. No.: WO2014/078478
PCT Pub. Date: May 22, 2014

(65) Prior Publication Data
US 2015/0284177 A1 Oct. 8, 2015

Related U.S. Application Data

(60) Provisional application No. 61/726,554, filed on Nov. 14, 2012.

(51) Int. Cl.
| | | |
|---|---|---|
| *B65D 83/22* | (2006.01) | |
| *B05B 11/00* | (2006.01) | |
| *A61M 15/00* | (2006.01) | |
| *A61M 15/08* | (2006.01) | |
| *B65D 83/14* | (2006.01) | |

(52) U.S. Cl.
CPC ......... *B65D 83/22* (2013.01); *A61M 15/0001* (2014.02); *A61M 15/08* (2013.01); *B05B 11/0027* (2013.01); *B05B 11/3059* (2013.01); *B65D 83/757* (2013.01)

(58) Field of Classification Search
CPC .. B65D 83/22; B65D 83/757; A61M 15/0001; A61M 15/08; B05B 11/0027
USPC ......... 222/153.04, 153.06, 153.07, 222/153.11–153.14, 321.6, 321.7–321.9, 222/321.1, 383.1, 383.3, 522–525
See application file for complete search history.

(56) References Cited

U.S. PATENT DOCUMENTS

| | | | | |
|---|---|---|---|---|
| 2,980,302 A | * | 4/1961 | Rasmussen | G01F 11/263 |
| | | | | 222/453 |
| 3,955,716 A | * | 5/1976 | Goncalves | B65D 83/40 |
| | | | | 215/256 |
| 4,147,280 A | | 4/1979 | Spatz | |

(Continued)

FOREIGN PATENT DOCUMENTS

| | | |
|---|---|---|
| CN | 101238048 A | 8/2008 |
| EP | 1829791 A1 | 9/2007 |

(Continued)

*Primary Examiner* — Donnell Long
(74) *Attorney, Agent, or Firm* — WestRock Intellectual Property Group

(57) ABSTRACT

A child-resistant feature or lock for a sprayer including a collar and a sleeve wherein the sleeve may be rotated from a locked position to an unlocked position to allow actuation of an actuator and pump for distribution of a product from a container to which the child-resistant feature is mounted.

16 Claims, 15 Drawing Sheets

(56) References Cited

U.S. PATENT DOCUMENTS

| | | | |
|---|---|---|---|
| 4,735,346 A | | 4/1988 | Stoody |
| 6,164,498 A | * | 12/2000 | Faughey ............ B05B 11/3008 222/153.13 |
| 6,708,846 B1 | | 3/2004 | Fuchs |
| 7,044,341 B2 | * | 5/2006 | Sanchez ............ B05B 11/0027 222/321.6 |
| 2007/0138207 A1 | | 6/2007 | Bonney |
| 2008/0023498 A1 | * | 1/2008 | Bertin ................ B05B 11/0032 222/402.12 |
| 2009/0120963 A1 | | 5/2009 | Bae |
| 2010/0206907 A1 | * | 8/2010 | Angus ................ B65D 83/206 222/153.11 |

FOREIGN PATENT DOCUMENTS

| | | |
|---|---|---|
| WO | WO 2008/010640 | 1/2008 |
| WO | WO 2010/121264 | 10/2010 |

\* cited by examiner

CHILD RESISTANT PUMPS

BACKGROUND OF THE INVENTION

Field of the Invention

Embodiments of the invention relate to child-resistant features or locking features for pumps and more particularly, to child resistant features and locks for use with nasal or vertically actuated pumps.

State of the Art

Various pump devices are used with pharmaceutical and other products to deliver a pharmaceutical agent in a desired manner. For instance, nasal pumps may be used to deliver a nasal spray into a users' nasal passageway for delivery of a pharmaceutical or other agent. In other instances, a pump may deliver one or more drops of fluid as desired by a user.

Child-resistant features—sometimes called CR features—may be incorporated with pumps and pump devices to limit access to the contents of the pump or to inhibit the use of a pump until the child-resistant feature is overcome. Such features are often used to prevent accidental ingestion of a drug or pharmaceutical agent by children.

Although various child-resistant features exist and may be incorporated with packaging and pumps, new and improved child-resistant features, and pumps incorporating such features, are desirable.

BRIEF SUMMARY OF THE INVENTION

According to certain embodiments of the invention, a sprayer—such as a nasal sprayer—includes one or more child resistant features or locking features which may selectively prevent or allow actuation of the sprayer. In some embodiments, a child resistant feature may include a collar secured to a container or bottle and a sleeve associated with the collar such that the sleeve may move from a locked position, preventing actuation of an actuator in communication with a pump, to an unlocked position allowing an actuator to be actuated.

According to some embodiments of the invention, a collar may include one or more bosses and a sleeve may include one or more grooves, tracks, slides or other features that mate with the one or more bosses to facilitate movement of the sleeve relative to the collar. In some embodiments, one or more retaining lugs may be configured in the sleeve to mate with, lock with, or engage one or more bosses on the collar such that the sleeve is locked against the collar and requires flexing to disengage the bosses from the lugs. In some embodiments, such disengagement may be accomplished by applying a force to the sleeve such that the sleeve flexes and the retaining lugs disengage from the bosses. According to some embodiments of the invention, a sleeve may include one or more bosses or locking lugs and a corresponding collar may include one or more tracks defined by one or more guide rails, grooves, tracks, slides or other features along which the one or more bosses or locking lugs may slide or move, controlling movement of the sleeve in relation to the collar. In some embodiments, one or more retention lugs in a track of a collar may interact with a boss on a sleeve thereby preventing movement of the sleeve relative to the collar until such time that the sleeve is deformed sufficiently to allow the boss to pass by the one or more retention lugs.

BRIEF DESCRIPTION OF THE DRAWINGS

While the specification concludes with claims particularly pointing out and distinctly claiming particular embodiments of the present invention, various embodiments of the invention can be more readily understood and appreciated by one of ordinary skill in the art from the following descriptions of various embodiments of the invention when read in conjunction with the accompanying drawings in which:

DETAILED DESCRIPTION OF THE INVENTION

According to various embodiments of the invention, a lock or a child-resistant feature may be fitted to, attached, or otherwise incorporated with a container or bottle and a pump to limit or inhibit actuation of the pump. In some embodiments of the invention, a lock or child-resistant feature may also include one or more tamper evident features capable of indicating whether or not a pump, container, or bottle to which the child-resistant feature or lock is attached has been compromised.

Figure 11:
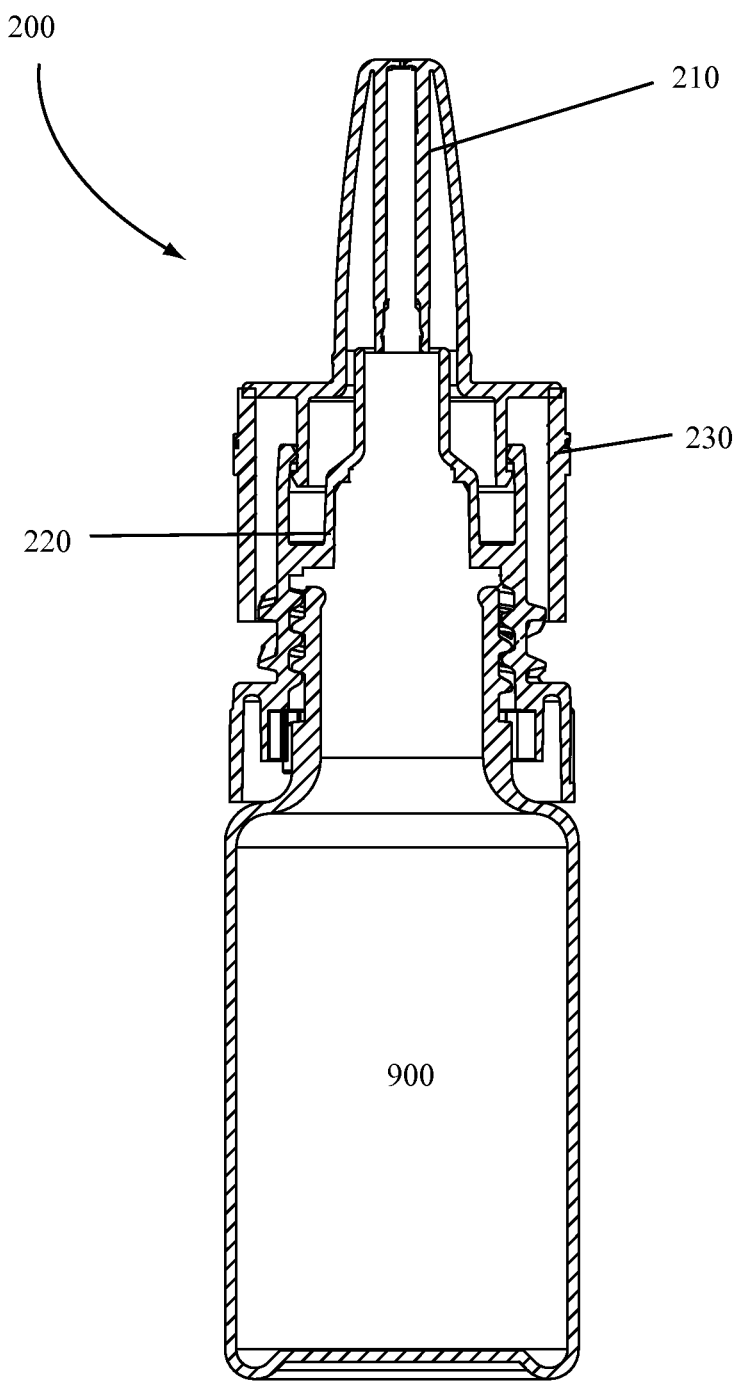
FIG. 11 illustrates a pump according to various embodiments of the invention.

While various embodiments of the invention are described with respect to a "child-resistant feature" it is understood that such feature may instead be a locking
} feature or other feature which may hinder or prevent access to the actuation of a pump by a user. Features need not pass "child-resistant" testing "senior friendly" testing or other certification in order to be considered part of the present invention. For instance, a locking feature as illustrated in FIG. 11 may not pass "child-resistant" or "senior friendly" testing or certification. Thus, "child-resistant feature," "senior friendly feature" and "locking feature" may be used interchangeably herein and such use is not intended to limit the features of the various embodiments of the invention.

Figures 1, 2:
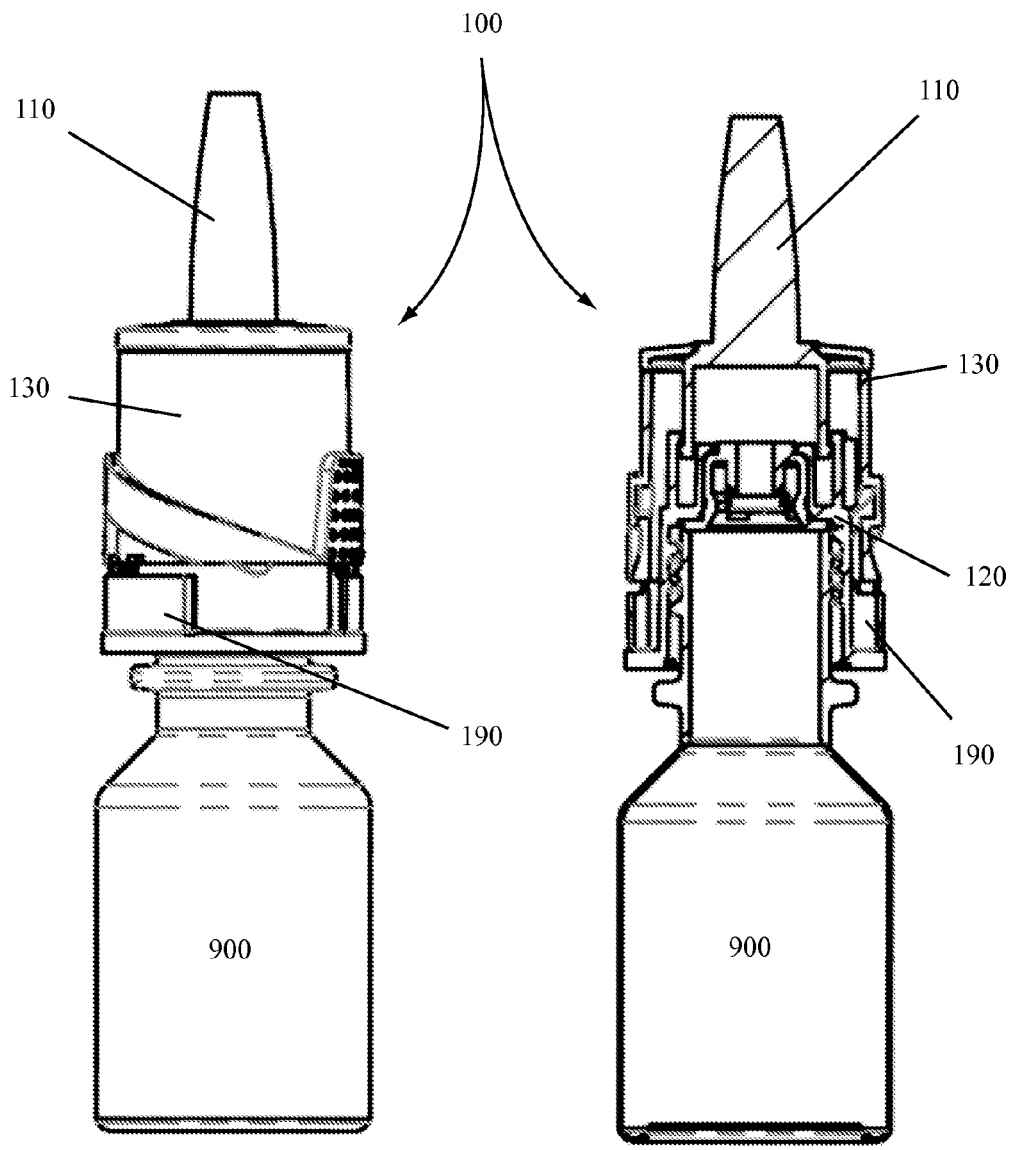
FIG. 1 illustrates a pump according to various embodiments of the invention.
FIG. 2 illustrates a cross-sectional view of the pump illustrated in FIG. 1.

A sprayer 100 according to various embodiments of the invention is illustrated in FIG. 1. As illustrated, the sprayer 100 may include a container 900 or bottle, an actuator 110 in communication with the container 900, a collar 120 fixed to the container 900 between the container 900 and actuator 110 and a sleeve 130 moveably fixed to, or positioned on, the collar 120. In some embodiments of the invention, a tamper evident feature may also be incorporated with the sprayer 100 such as the tear strip 190 as illustrated in FIG. 1.

Various embodiments of the invention are described herein with respect to a sprayer 100 having a nasal spray actuator 110 as illustrated in the various figures. While the illustrations depict an actuator 110 typically used for nasal sprayers or configured for delivery of a nasal spray, it is understood that the actuator 110 need not be of the nasal sprayer type. Instead, for example, a finger pump actuator or fine mist spray pump actuator could be substituted for the nasal actuator 110. Furthermore, various pumps or pump mechanisms may be incorporated with various embodiments of the invention and such embodiments are not limited by the type of pump used or by the exemplary pump illustrated in the figures.

According to certain embodiments of the invention, a collar 120 is attached to the container 900. In some embodiments, the collar 120 may be attached to the container 900 such that the collar 120 may be removed from the container 900. In other embodiments, the collar 120 may be fixed to the container 900 such that the collar 120 may not be removed from the container 900 or may not be removed from the container 900 without destruction or deformation of the collar 120 or container 900. Connection of a collar 120 to a container 900 may be accomplished using known connection methods and configurations. For example, a collar 120 may be connected to a container 900 by screw-type threading, ferrule fitments, snap fitments, bayonet connections, welding, adhesive, or any other known fitment method or product commonly used to attach a pump or closure to a container 900. In some embodiments of the invention, a container 900 neck may include features to retain fixation of the collar 120 to the container 900. For example, the container 900 may include ratchet features about a neck of the container 900 which may engage with and lock with ratchet features on an interior surface of the collar 120. In some embodiments, such ratchet features may prevent removal of the collar 120 from the container 900 once assembled.

According to various embodiments of the invention, a collar 120 may have a generally cylindrical shape. One or more bosses 122 or lugs may be positioned on an exterior surface of the collar 120. For example, according to some embodiments of the invention, two bosses 122 may be located on an outer suraice of the collar 120 such that each of the bosses 122 is 180 degrees away from the other boss 122 or, in other words, on opposite sides of the collar 120.

Figures 9, 10:
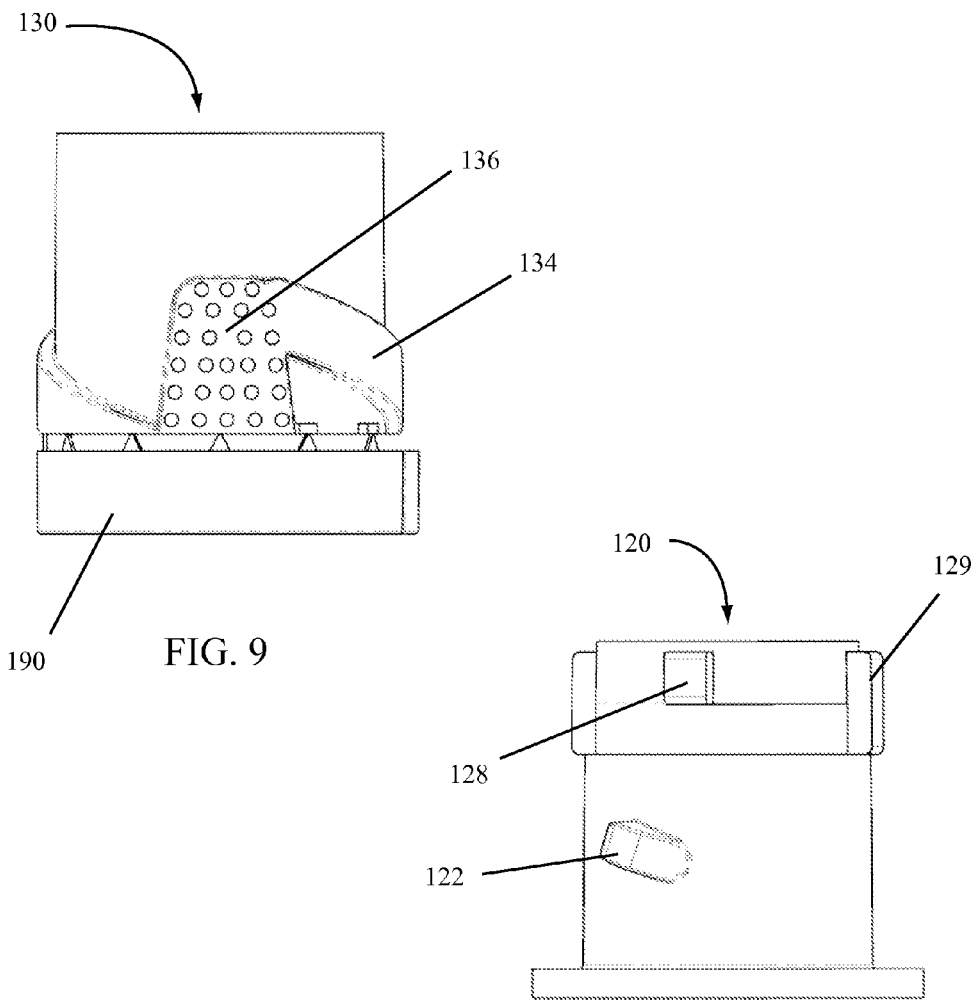
FIG. 9 illustrates a sleeve according to various embodiments of the invention.
FIG. 10 illustrates a collar according to various embodiments of the invention.

As illustrated in FIG. 10, a boss 122 may be angled with respect to a parallel plane across the bottom of the collar 120. A boss 122 may also include various shapes or geometries as desired. For instance, a boss 122 may include a ramp portion as illustrated in FIG. 10. A ramp portion, in some embodiments of the invention, may facilitate the locking of a sleeve 130 relative to the collar 120. For example, the ramp portion of the boss 122 illustrated in FIG. 10 may slope from a high point to a tow point at the location closest to the base of the collar 120 as illustrated.

In some embodiments of the invention, a collar 120 may also include one or more stop lugs 128 or alignment lugs 129 or any combination thereof. The stop lugs 128 and alignment lugs, if included, may be on an exterior surface of the collar 120. In some embodiments, the one or more stop lugs 128 or alignment lugs 129 may be positioned near the actuator side of the collar 120 nearest the actuator 110 and firthest from the container 900. In some embodiments, stop lugs 128 may also act as alignment lugs 129.

A sleeve 130 according to various embodiments of the invention is illustrated in FIG. 9. As illustrated, a sleeve 130 may have a generally cylindrical shape or tapering cylindrical shape. A sleeve 130 may also include one or more cam grooves 134 and one or more finger pads 136. The one or more cam grooves 134 may be in communication with the one or more finger pads 136. A cam groove 134 may include a groove in an interior wall surface of the sleeve 130 and may be sloped to facilitate movement of a sleeve 130 relative to a collar 120.

Figures 6, 7:
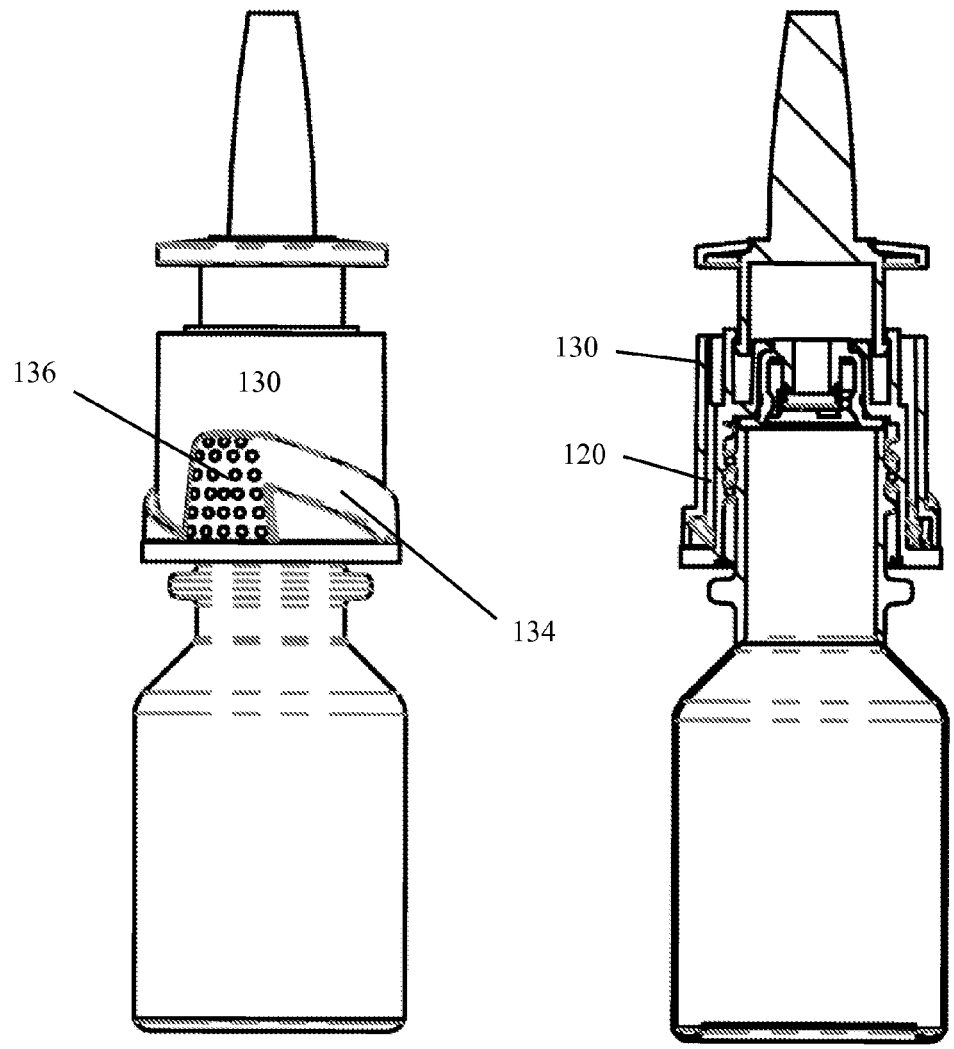
FIG. 6 illustrates a pump according to various embodiments of the invention.
FIG. 7 illustrates a pump according to various embodiments of the invention.
Figure 8:
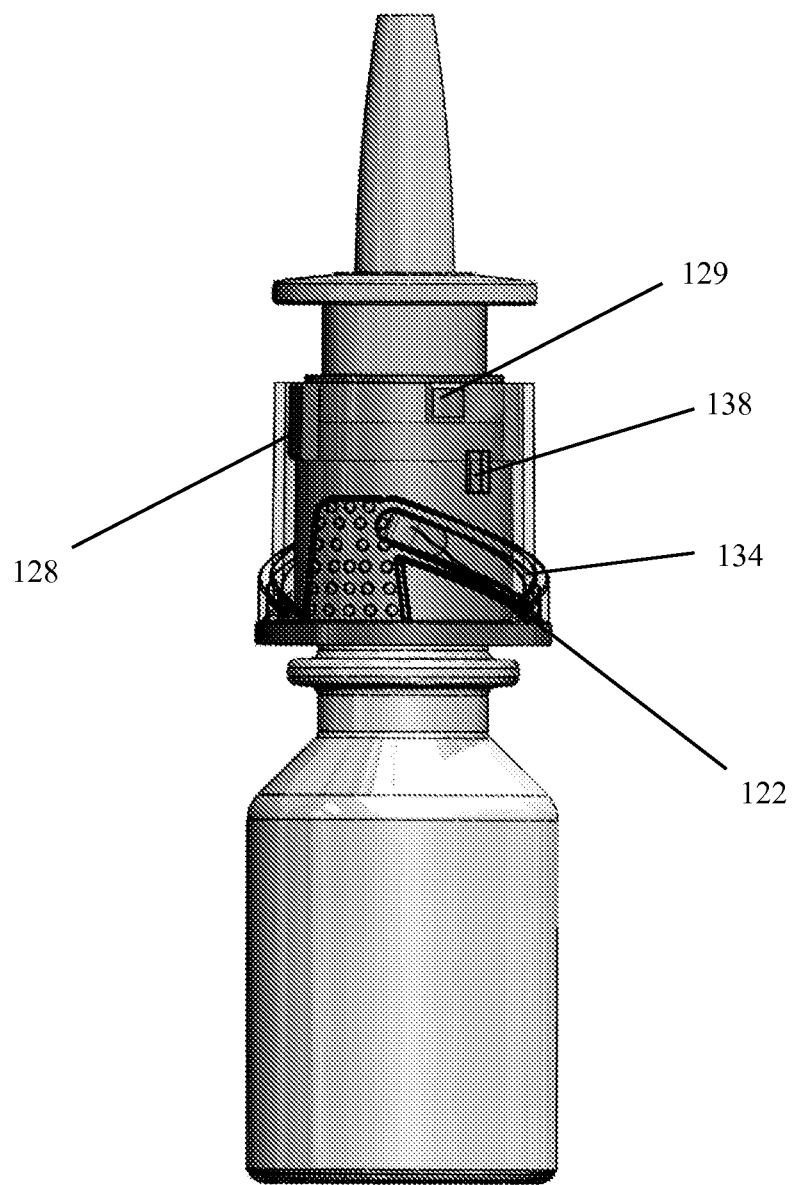
FIG. 8 illustrates a pump according to various embodiments of the invention.

A sleeve 130 according to various embodiments of the invention may move relative to the collar 120. For example, the sleeve 130 may move from a locked position to an unlocked position. An example of a sleeve 130 in a locked position is illustrated in FIGS. 1 through 5. An example of a sleeve 130 in an unlocked position is illustrated in FIGS. 6 through 8. In a locked position, sleeve 130 inhibits or prevents actuator 110 from being actuated. In an unlocked position, sleeve 130 is positioned such that an actuator 110 may be actuated.

Figure 3:
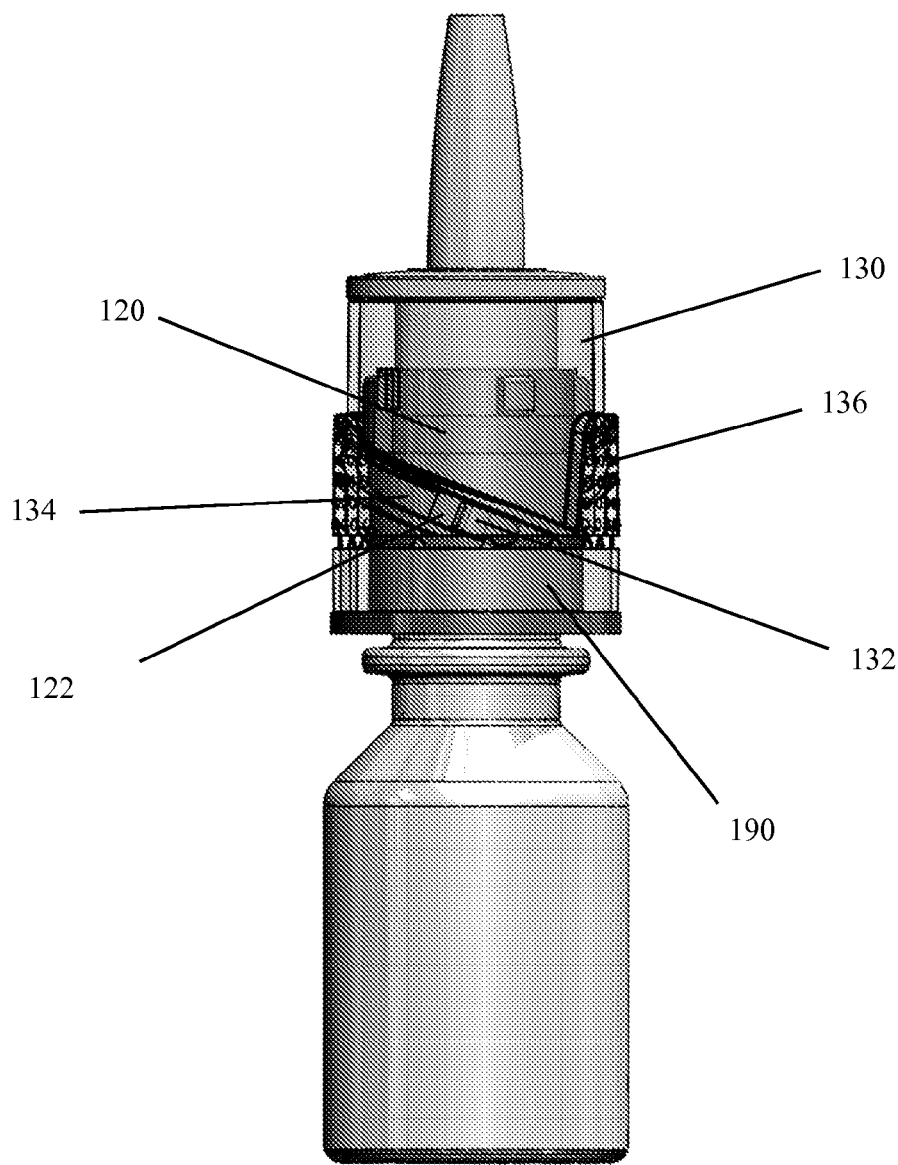
FIG. 3 illustrates a pump according to various embodiments of the invention.

A sleeve 130 according to various embodiments of the invention may include one or more retention lugs 132 positioned within the one or more cam grooves 134. For example, as illustrated in FIG. 3, a retention lug 132 positioned in a cam groove 134 may abut against a collar boss 132 when the sleeve 130 is in a locked position. Interaction of the retention lug 132 with the boss 122 may prevent the sleeve 130 from being moved relative to the collar 120.

A sleeve 130 in a locked position may be disengaged from the locked position by squeezing the sleeve 130 or applying force to the sleeve 130 at the finger pads 136. The finger pads 136 may be positioned 90 degrees from the retention lugs 132 such that when a force is applied to the finger pads 136 the sleeve 130 shape is altered to be more oval in nature such that the retention lugs 132 disengage from the boss 122 and allow the sleeve 130 to be rotated relative to the collar 120. Thus, as force is applied to finger pads 136, sleeve 130 may be rotated such that the retention lugs 132 disengage from the collar 120 bosses 122 and allow rotation of the sleeve 130 relative to the collar 120. During rotation of the sleeve 130 the bosses 122 may track along the cam groove 134, which may guide movement of the sleeve 130.

To lock a sleeve 130 that is in an unlocked position, the sleeve 130 may be rotated an opposite direction to the point where the retention lugs 132 engage with the bosses 122 to lock the sleeve 130 relative to the collar 120.

In some embodiments of the invention, an interior surface of a sleeve 130 may include one or more sleeve stop lugs 138 as illustrated in FIG. 8. The one or more sleeve stop lugs 138 may abut against or contact the one or more collar stop lugs 128 or alignment lugs 129 to prevent the sleeve 130 from being rotated past the lock position or off of the sprayer 100. For example, as the sleeve 130 in FIG. 8 is rotated back to a locked position, the one or more sleeve stop lugs 138 rotate into engagement or abutment with the one or more collar stop lugs 128 or alignment lugs 129. In various embodiments of the invention, the sleeve stop lugs 138 and the collar stop lugs 128 may be sized and positioned to accomplish a hard stop and prevent rotation after a locked position is reached. In some embodiments of the invention, the sleeve stop lugs 138 and collar stop lugs 128 or alignment lugs 129 may also add structural integrity to the sleeve 130 and collar 120 interactions. For example, the collar stop lugs 128 or alignment lugs 129 may contact the sleeve 130 interior surface to prevent movement or pinching of the sleeve 130 against the collar 120 when a force is applied.

According to various embodiments of the invention, a tamper evident feature may include a tear strip 190 as illustrated FIGS. 1 through 3 and 9. A tear strip 190 may be fixed to a sleeve 130 or molded therewith and may include a tab which may be grabbed or gripped by a user and pulled. Attachments between the tear strip 190 and the sleeve 130 may break away as the tab is pulled, thereby allowing the tear strip 190 to be removed from the sleeve 130.

According to other embodiments of the invention, a tamper evident feature may include a removable shrink wrap film about the actuator 110, or portion thereof, and sleeve 130. In other embodiments, a removable shrink wrap film may be positioned about at least a portion of the actuator 110, the sleeve 130 and a portion of the collar 120 or the collar 120 and the container 190. Other tamper evident features or structures as known in the art could also be incorporated with various embodiments of the invention.

Figures 4, 5:
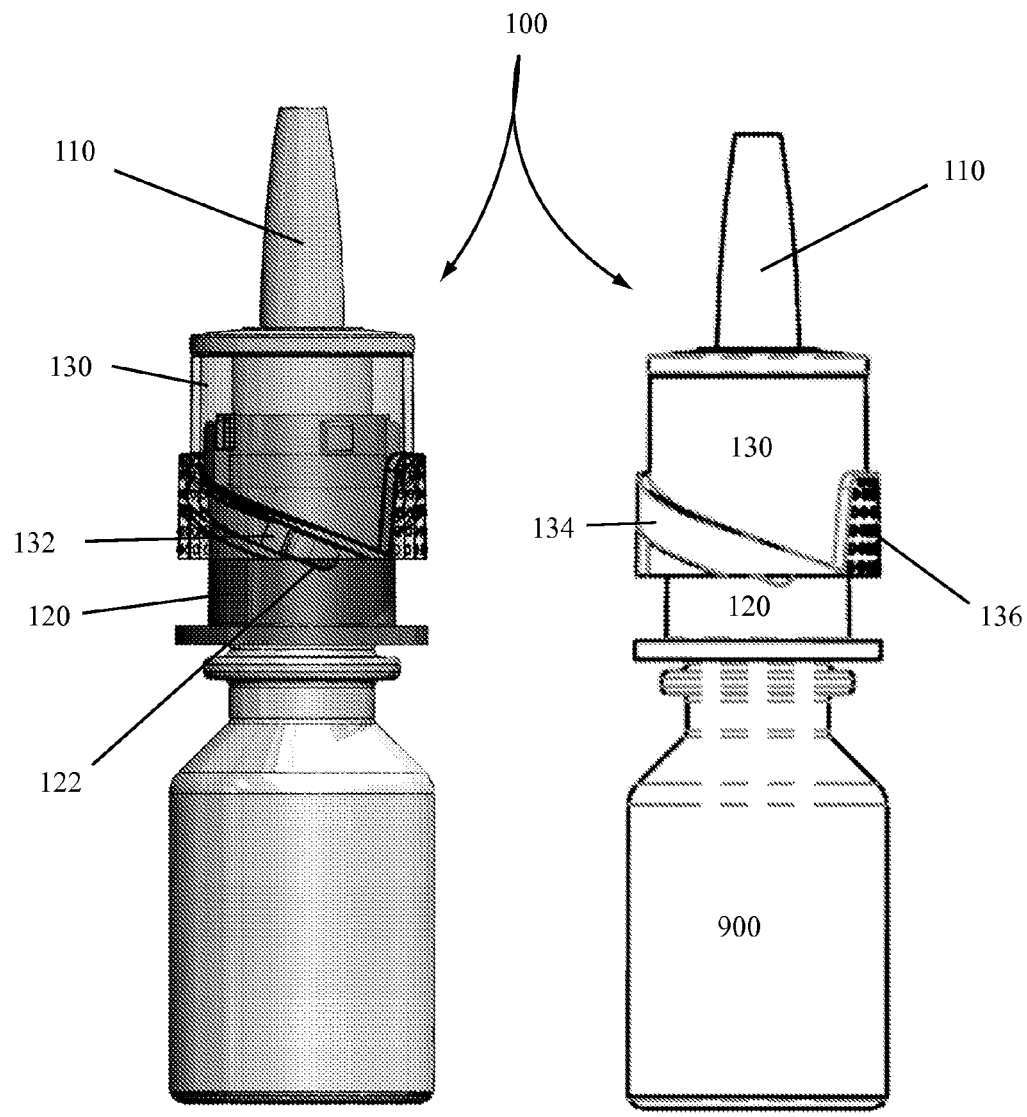
FIG. 4 illustrates a pump according to various embodiments of the invention.
FIG. 5 illustrates a pump according to various embodiments of the invention.

An assembled sprayer 100 according to various embodiments of the invention is illustrated in FIGS. 1 and 3. As illustrated, the sprayer 100 includes a tear strip 190 which prevents movement of the sleeve 130 relative to the collar 120 until at least the tear strip 190 is removed. Once removed, as illustrated in FIGS. 4 and 5, a force may be applied to the sleeve 130 at the one or more finger pads to elongate or disfigure the sleeve 130 into an oval shape, thereby disengaging the retention tugs 132 from the one or more bosses 122 and allowing the sleeve 130 to be rotated toward the container 900 and away from the actuator 110 about the collar 120.

Once rotated, the sleeve 130 is in an unlocked position as illustrated in FIGS. 6 through 8. In the unlocked position, the actuator 110 may be actuated, allowing a product to be dispersed from the container 900 through a pump associated with the sprayer 100.

The sleeve 130 may be rotated back into a locked position by twisting the sleeve 130 in the opposite direction of that used to unlock the sprayer 100. In some embodiments, when re-locked, engagement of the retention lugs 132 with the bosses 122 may make an audible noise or provide tactile feedback to let a user know that the sleeve 130 is again in a locked position. In addition, one or more stop lugs 138 may engage with or abut against one or more collar stop lugs 128 to prevent over-rotation of the sleeve 130 back into a locked position.

While various embodiments of the invention have been described with a cam groove 134 on the sleeve 130 and one or more collar bosses 122 mated therewith, it is understood that in other embodiments one or more cam grooves could be integrated with the collar 120 and one or more bosses integrated with the sleeve 130.

For example, a sprayer 200 according to other embodiments of the invention is illustrated in FIG. 11. As illustrated, the sprayer 200 includes a container 900 or bottle, a collar 220 attached to the container 900, a sleeve 230 moveably fixed to, attached to, or positioned on, the collar 220 and an actuator 210 in communication with the collar 220. While not illustrated in FIG. 11, some embodiments of the invention may also include a tamper evident feature such as a tear strip to indicate whether or not the collar 220 has been removed from the bottle 900.

According to some embodiments of the invention, a collar 220 is attached to the container 900 by a screw-type or threaded attachment as illustrated in FIG. 11. In other embodiments, a collar 220 may be attached to a container 900 by a bayonet-type system or snap-fit system as known in the art. Depending on the desired use for the sprayer 200, a collar 220 may be attached to the container 900 such that it may be removed therefrom. In other embodiments of the invention, a collar 220 may be attached to a container 900 such that it cannot be removed or cannot be removed without destroying or deforming the collar 220 or container 900. For example, a collar 220 such as that illustrated in FIG. 11 may include one or more collar ratchet teeth 290 as illustrated 18 through 20. The one or more collar ratchet teeth 290 may mate with one or more container ratchet teeth such that once assembled to the container 900, the one or more collar ratchet teeth 290 interact with the one or more container ratchet teeth to prevent rotation of the collar 220 off of the container 900.

Figure 19:
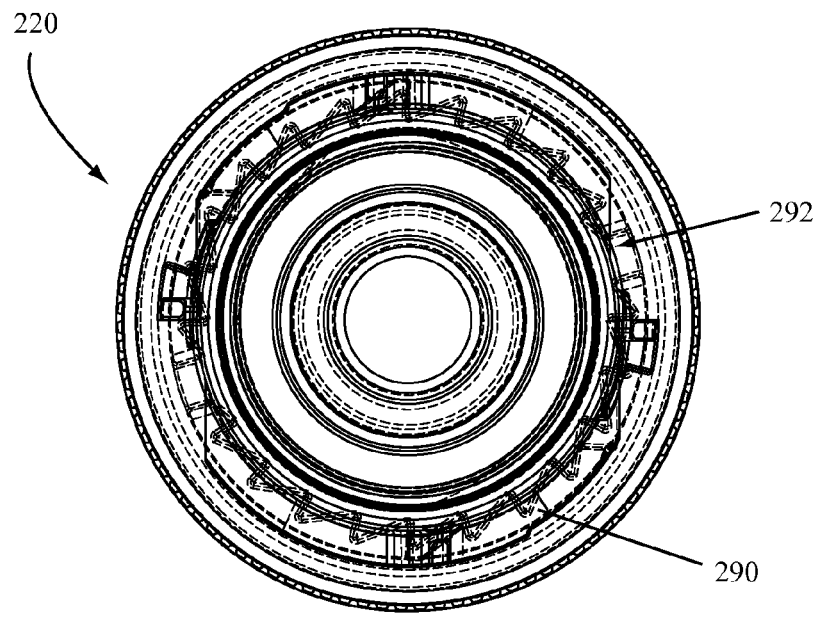
FIG. 19 illustrates a top-down view of a collar of a pump according to various embodiments of the invention.
Figure 20:
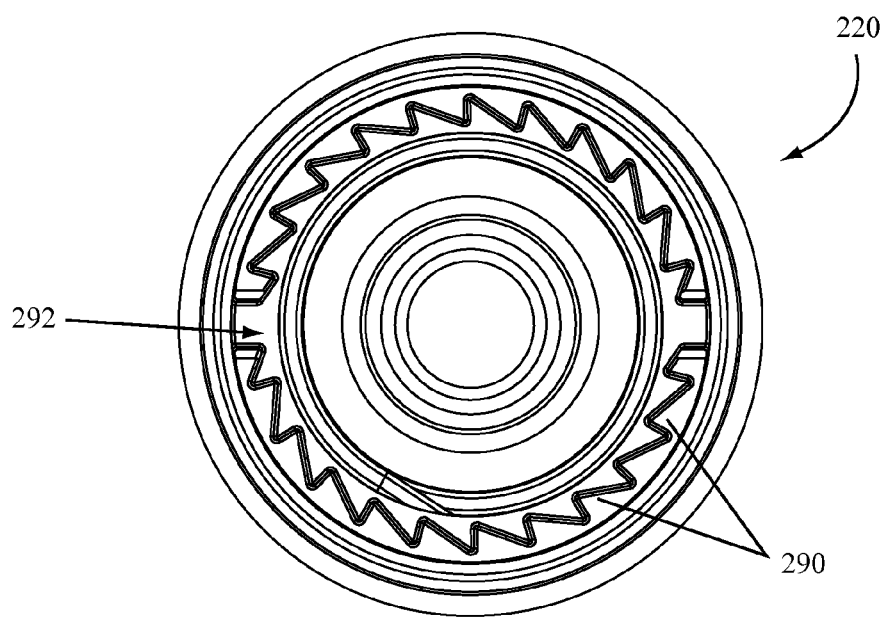
FIG. 20 illustrates a bottom-up view of a collar of a pump according to various embodiments of the invention.

According to some embodiments of the invention, a collar 220 may include one or more collar ratchet teeth 290 and one or more ratchet gaps 292. As illustrated in FIGS. 19 and 20, a collar 220 according to one embodiment may include two ratchet gaps 292. A ratchet gap 292 is an open space or break in the ratchet pattern of the collar ratchet teeth 290 as illustrated. The ratchet gap 292 may be used to orient a collar 220 for assembly or attachment to a container 900. For example, the positioning of the one or more ratchet gaps 292 may be sensed or "visualized" by traditional automation equipment on an assembly line and the collar 220 moved into a desired position for assembly to a container 900. In other instances, a track for moving a collar 220 along assembly equipment may include fittings to mate with the one or more ratchet gaps 292 such that collars 220 fed to the track may be rotated until the one or more ratchet gaps 292 seats on the fittings such that the collar 220 is aligned on the track in a desired position for picking, assembly with other parts of the sprayer 200, or for attachment to a container 900.

Figure 18:
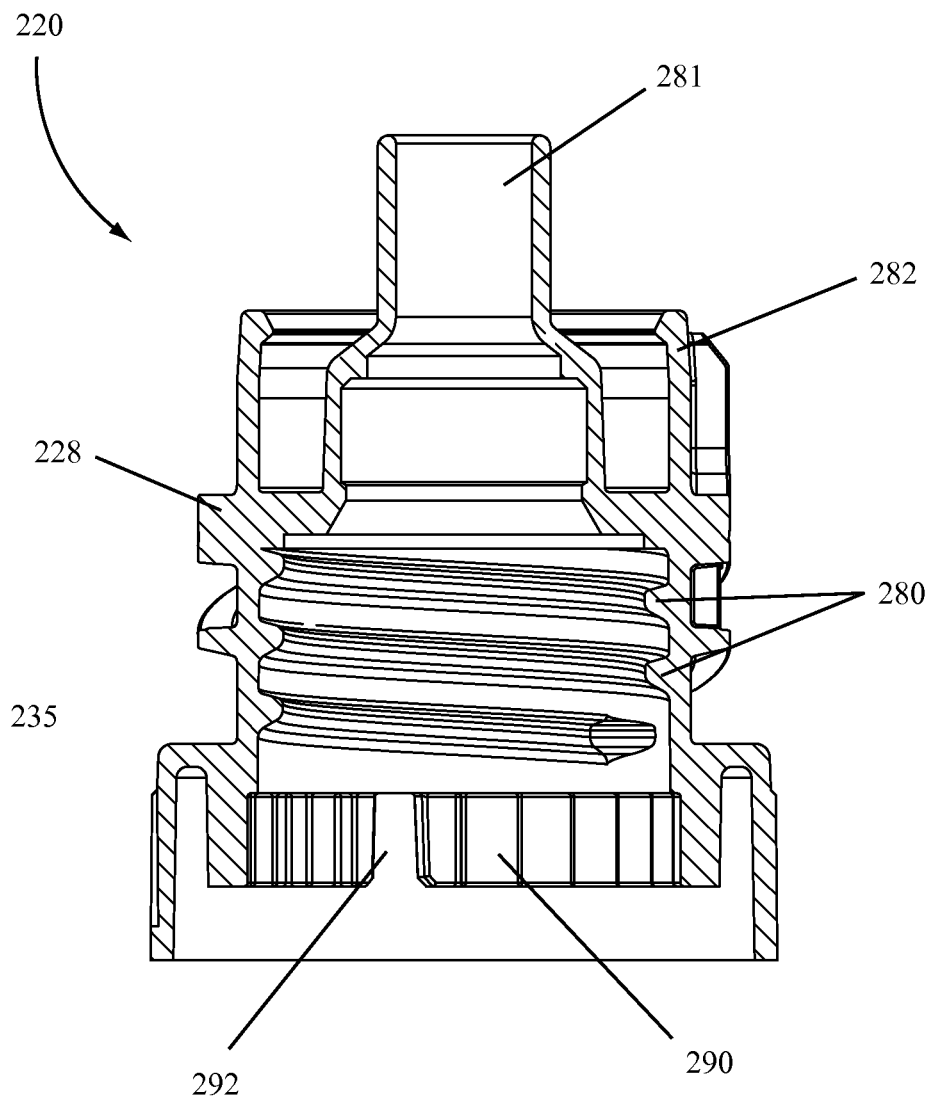
FIG. 18 illustrates a cross-sectional view of a collar of a pump according to various embodiments of the invention.

A collar 220 for a sprayer 200 according to various embodiments of the invention is illustrated 16 through 20. As illustrated, a collar 220 may be generally cylindrical in shape. A connection mechanism—such as a threaded connection system, a bayonet connection system, a snap-fit connection system, or other connection system—may be generally oriented on an interior portion of the collar 220. For example, as illustrated in FIG. 18, an interior surface of the collar 220 may include one or more threads 280 which may be used to thread the collar 220 onto a container 900 having a corresponding threaded attachment feature. The use of connection mechanisms is known in the art.

According to some embodiments of the invention, a collar 220 may include a skirt extending below the connection mechanism. As illustrated in FIG. 18, the skirt may include ratchet teeth 290 and ratchet gaps 292 used for securing the collar 220 to a container 900.

In some embodiments of the invention, a collar 220 may also include a second, outer skirt extending downward from, or below, the connection mechanism as illustrated in FIG. 18. The second, outer skirt may overlie and cover the skirt when the collar 220 is assembled with a container 900. In some instances, the second, outer skirt may protect the skirt and prevent access to security features—such as ratchet teeth 290—on the skirt so that a user may not easily remove or tamper with the connection of the security features with a container. For example, as illustrated in FIG. 11, the second, outer skirt of the collar 220 extends down to an upper surface of the container 900 such that it is difficult for a user to contact or interact with the location where the ratchet teeth 290 interact with the container 900. In some instances, the outer skirt may contact a container 900 once assembled such that only deformation or destruction of the container 900 or collar 220 will allow the disengagement of the collar 220 from the container 900. Such features may help improve the "child-resistant" features of a sprayer 200 according to embodiments of the invention.

A collar 220 according to various embodiments of the invention may also include a track 234 on an outer surface of the collar 220. As illustrated in Ms, 16 and 17, a track 234 may be defined by two or more guide rails 235. An upper guide rail 235 and a lower guide rail 235 may define a channel or track 234 along which a boss 222 of a sleeve 230 may travel. An upper guide rail 235 may slope upwards from a lower portion of the collar 220 and then angle vertically to form an alignment rib 229 as illustrated. A tower guide rail 235 may continue an upward slope from a lower portion of the collar 220. One or more retention lugs 232 may be positioned within a portion of the track 234. A retention lug 232 may also include one or more sloped surfaces to facilitate interaction with a boss 222 of a sleeve 230.

An alignment rib 229, according to various embodiments of the invention, may be used—or may facilitate—orientation of a collar 220 during assembly of a sprayer 200. For example, during an assembly process, an alignment rib may be "visualized" or identified by the assembly equipment using known "visualization" techniques and then aligned appropriately based on the visualization for further assembly.

According to various embodiments of the invention, a collar 220 may include one or more tracks 234. As illustrated in FIGS. 16 through 19, a collar 220 may include two separate tracks 234 opposite each other on the outer surface of the collar 220. At the base of a track 234, a collar 220 may include one or more positive stops 287. A positive stop 287 may be in place such that it engages a boss 222 of a sleeve 230 when the sleeve 230 is in an open position. Engagement of the boss 222 with the positive stop 287 may prevent the sleeve 230 from jumping off of the track 234.

Figure 16:
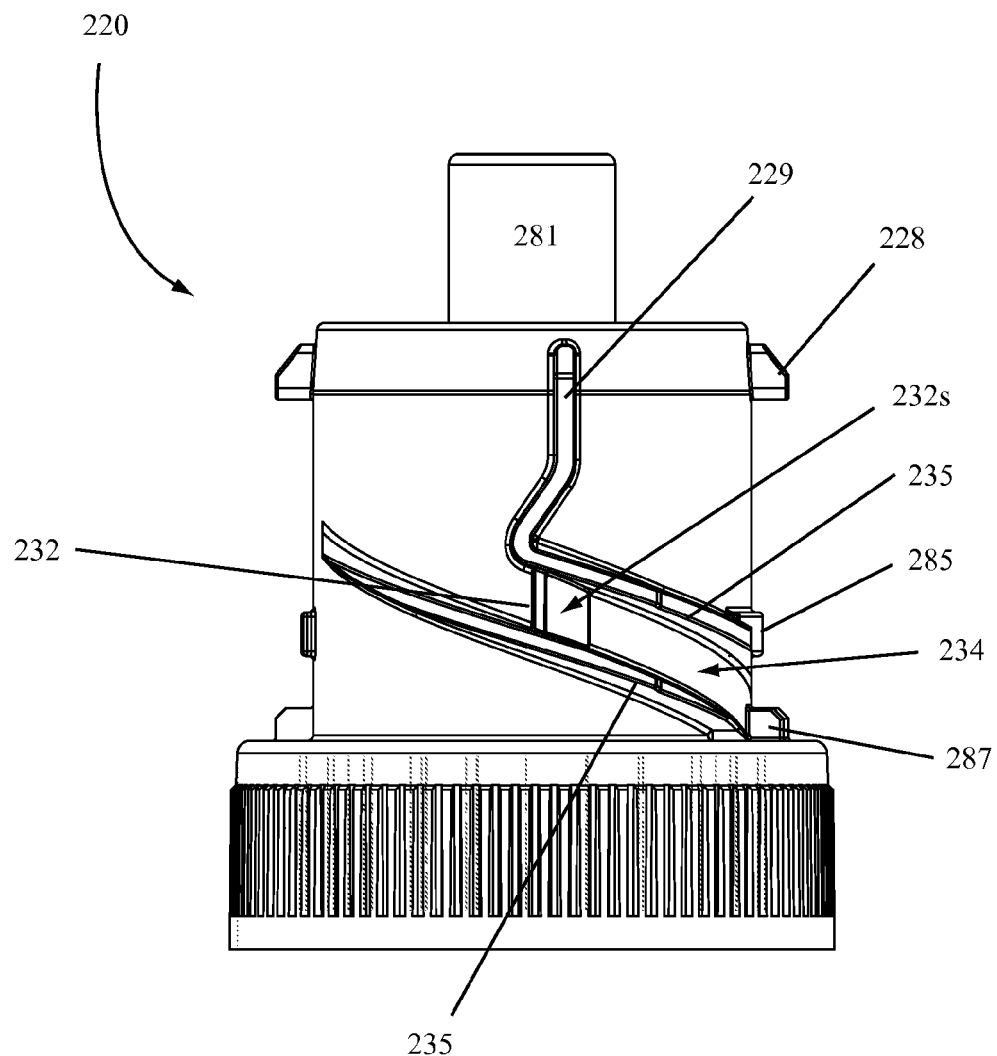
FIG. 16 illustrates a collar of a pump according to various embodiments of the invention.
Figure 17:
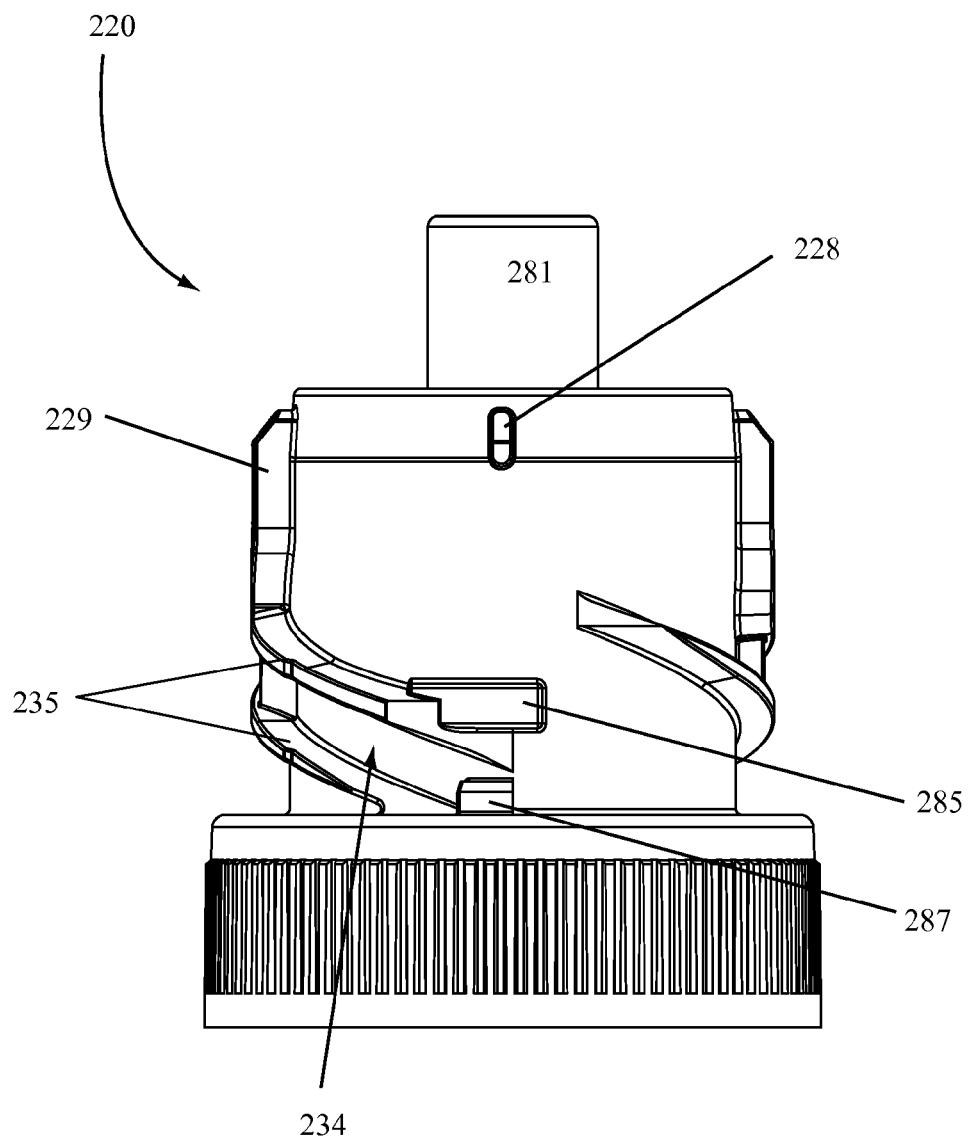
FIG. 17 illustrates a collar of a pump according to various embodiments of the invention.

One or more pinch restrictors 285 may also be integrated with the one or more tracks 234 or positioned near the one or more tracks as illustrated in FIGS. 16 and 17. A pinch restrictor 285 may be configured to allow the sleeve 230 to be pinched at the one or more finger pads 236 to cause enough deformation of the sleeve 230 to allow a boss 222 to disengaged from a retention tug 232 but not allow enough deformation to allow a boss 222 to jump outside of the track 234 or over the guide rails 235.

A collar 220 according to various embodiments of the invention may also include one or more collar stop lugs 228 on an exterior surface thereof. The one or more stop lugs 228 may be positioned near the actuator end—or upper end—of the collar 220 opposite the skirts. The one or more stop tugs 228 may interact with one or more sleeve stop tugs 238 to prevent movement of a sleeve 230 relative to a collar 220. Stop lugs 228 may also be used for alignment purposes or aligning a collar 220 during assembly.

As illustrated in FIGS. 11 and 18, a collar 220 may include an upper skirt 282 extending upward towards a top portion of the collar 220. The upper skirt 282 may include a boss, lip, other feature to retain an actuator 210 on the collar 220. For example, as illustrated in FIG. 11, an actuator 210 may be assembled to a collar 220 such that when the actuator 210 is pushed vertically by a pump mechanism of the sprayer 200, a lip on the upper skirt 282 of the collar 220 may help prevent the actuator 210 from disassembling from the collar 220. In addition, the upper skirt 282 may provide a guide upon which the actuator 210 may move during actuation of a sprayer 200.

A collar 220 according to still other embodiments of the invention may also include an actuation stop 281 as illustrated in FIGS. 16 through 18. The actuation stop 281 may include a cylindrical, square, or other shaped extension off of a top end of the collar 220 and may be positioned inside of the upper skirt 282 of the collar 220. The actuation stop 281 may be sized such that a piston of a pump residing inside of the collar 220 does not extend beyond the upper opening of the actuation stop 281. With such configuration, if an actuator is disassembled from the collar 220 and upper skirt 282, the pump cannot be actuated with a finger because the piston lies below the upper opening of the actuation stop 281 which is small enough to prevent a user from manually actuating the sprayer 200.

As illustrated in FIG. 11, a sleeve 230 may be moveably attached to or in communication with a collar 220 according to various embodiments of the invention. For example, a sleeve 230 may include one or more bosses 222 or lugs positioned on an interior surface of the sleeve 230. The one or more bosses 222 may ride within a track 234 or cam groove within a collar 220. Positioning of the one or more bosses 222 within one or more tracks 234 may retain the sleeve 230 on the collar 220.

According to some embodiments of the invention, a sleeve 230 may have a generally cylindrical shape with an interior surface and an exterior surface and a first and second open end; the first open end being closest to the container 900 when assembled as part of a sprayer 200.

On an interior surface of the sleeve 230, one or more bosses 222 may be located. A boss 222 may project inwardly from the interior sleeve 230 surface towards a centerline of the sleeve 230. According to some embodiments of the invention, a sleeve 230 may include two bosses 222 on an interior surface thereof, wherein a first boss 222 is positioned on the interior surface directly opposite a second boss 222. In other embodiments, more than two bosses 222 could be included on an interior surface of the sleeve 230. In some embodiments, one or more bosses 222 may be positioned near the first open end of the sleeve 230. In other embodiments, one or more bosses 222 may be positioned near the second open end of the sleeve 230 or anywhere between the first open end and second open end. The one or more bosses 222 may be angled such that the bosses 222 may ride on a track 234 associated with a collar 220, the angle of the boss 222 positioning corresponding to the angle of incline of a track 234. For example, as illustrated in FIG. 14, a boss 222 may include an upper surface 222*a* and a lower surface 222*b*, each having a corresponding angle of incline as the upper surface 222*a* and lower surface 222*b* move from closer the first open end to the second open end.

Figure 12:
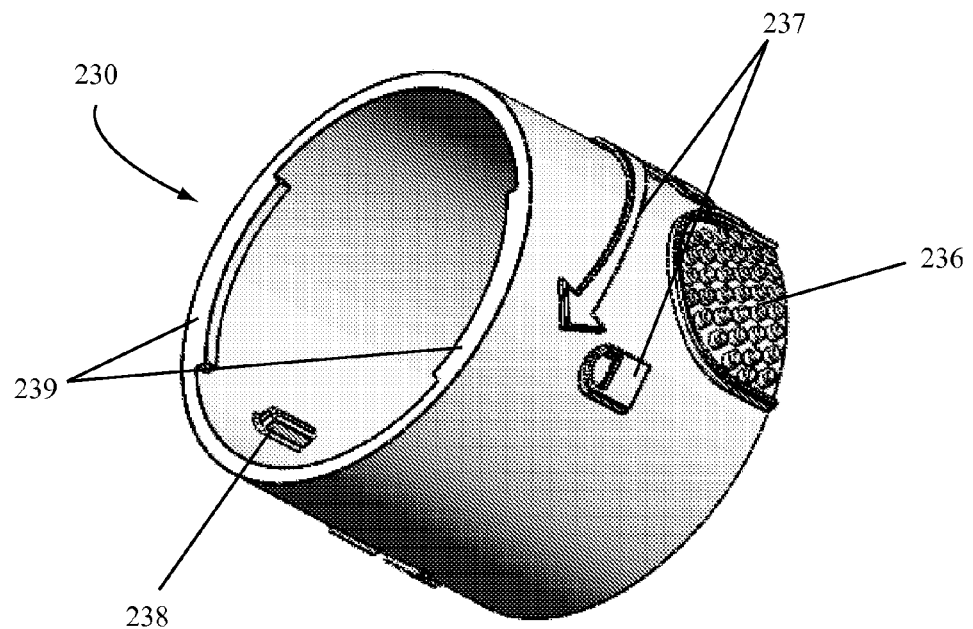
FIG. 12 illustrates a sleeve of a pump according to various embodiments of the invention.
Figure 14:
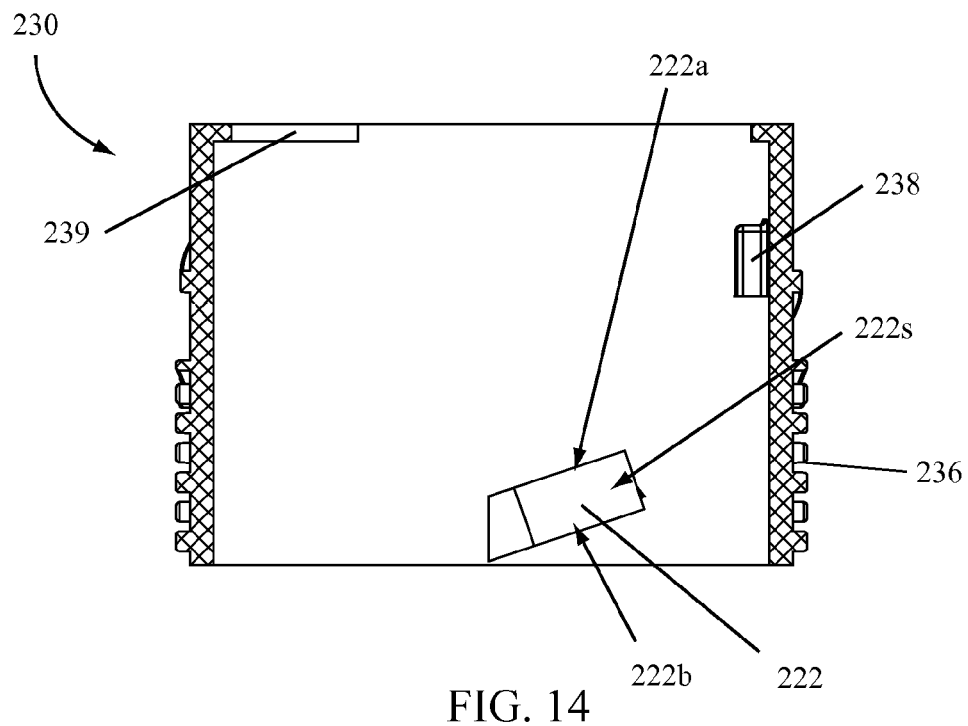
FIG. 14 illustrates a cross-sectional view of a sleeve of a pump according to various embodiments of the invention.
Figure 15:
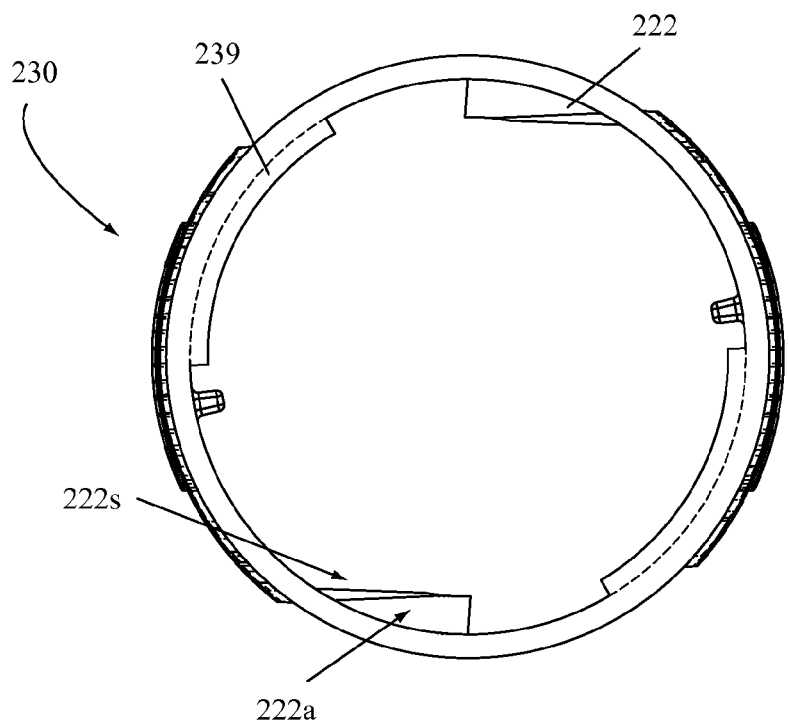
FIG. 15 illustrates a top-down view of a sleeve of a pump according to various embodiments of the invention.
Figure 21:
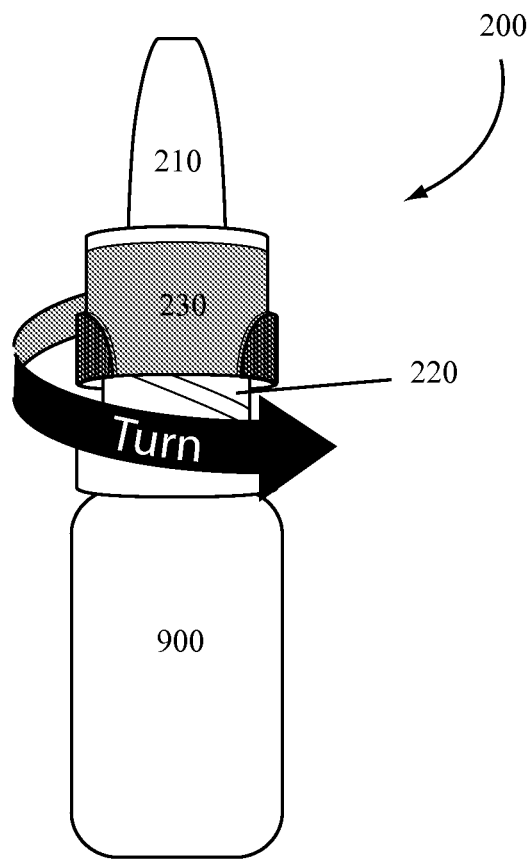
FIG. 21 illustrates a sprayer according to various embodiments of the invention in a closed or locked position.

A sleeve 230 according to various embodiments of the invention may also include one or more sleeve stop lugs 238 as illustrated in FIGS. 12, 14 and 15. The one or more sleeve stop lugs 238 may abut against or contact one or more collar stop lugs 228 or alignment ribs 229. Contact between the sleeve stop lug 238 and a collar stop lug 228 or alignment rib 229 may help prevent the sleeve 230 from being rotated past the lock position of off of the sprayer 200. For example, as a sleeve 230 is rotated into a locked position as illustrated in FIG. 21, one or more sleeve stop lugs 238 rotate into engagement or abutment with the one or more collar stop lugs 228 of alignment ribs 229. In various embodiments of the invention, the sleeve stop lugs 238 and the collar stop lugs 228 may be sized and positioned to accomplish a hard stop and prevent rotation after a locked position is reached. In some embodiments of the invention, the sleeve stop lugs 238 and collar stop lugs 228 or alignment ribs 229 may also add structural integrity to the sleeve 230 and collar 220 interaction, for example by preventing unwanted deformation of the sleeve 230 relative to the collar 220 except in the locked position when the finger pads 236 are being engaged to deform and disengage the sleeve 230 from a locked position.

A sleeve 230 according to various embodiments of the invention may also include one or more alignment rims 239 about an opening in the sleeve 230. Such features are illustrated, for example, in FIGS. 12, 14, and 15. The one or more alignment rims 239 may be used to orient a sleeve 230 during the assembly process such that a sleeve 230 may be "picked" or selected for assembly to a collar 220 and aligned appropriately with the collar 220 for assembly. For example, in order to align a sleeve 230 on a collar 220 such that oboes 222 of a sleeve 230 is oriented such that it can be positioned in a track 234 of the collar 220, an alignment rim 239 may be included on the sleeve 230, which alignment rim 239 allows automated assembly equipment to "visualize" and orient the sleeve 230 in an appropriate position to allow proper assembly of the sleeve 230 with a collar 220.

According to various embodiments of the invention, an exterior surface of a sleeve 230 may include one or more finger pads 236 as illustrated in FIGS. 12 through 15. In some embodiments, a sleeve 230 includes two finger pads 236 located on the exterior surface of the sleeve 230, the two finger pads 236 being opposite each other on the sleeve 230 as illustrated. In other embodiments, the finger pads 236 may be positioned in different locations as desired.

Figure 13:
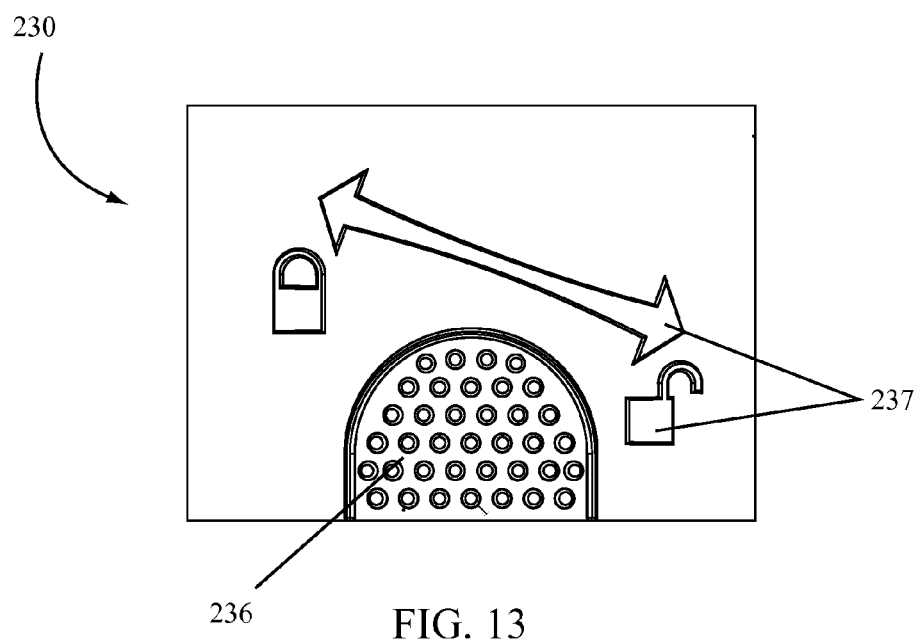
FIG. 13 illustrates a side-view of a sleeve of a pump according to various embodiments of the invention.

A sleeve 230 according to some embodiments of the invention may also include one or more visual cues 237 as illustrated in FIGS. 12 and 13. For example, as illustrated in FIG. 13, visual cues 237 may include embossed or raised images which may facilitate proper operation of a sleeve 230. In the case of the visual cues 236 illustrated, an arrow between a locked and an unlocked image of a lock indicates to a user that the sleeve 230 must be moved upward to lock the device and moved downward to unlock the device. Other visual cues may be included with various embodiments of the invention as desired.

Figure 22:
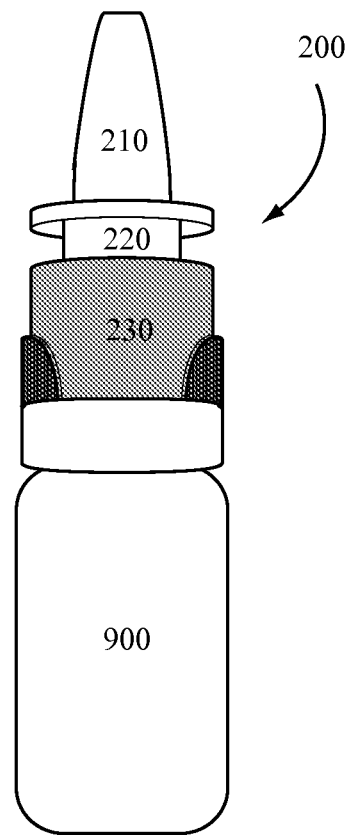
FIG. 22 illustrates a sprayer according to various embodiments of the invention in an open or unlocked position.

Operation of a sprayer 200 according to various embodiments of the invention is illustrated in FIGS. 21 and 22. A sprayer 200 in a locked position is illustrated in FIG. 21. In such configuration, the actuator 210 may not be actuated because the position of the sleeve 230 prevents actuation of the actuator 210. To move the sleeve 230 into an unlocked position as illustrated in FIG. 22, a user may pinch the sleeve 230—for example by pinching the finger pads 236 on the sleeve 220—to disengage the sleeve 230 from the collar 220, allowing rotation or turning of the sleeve 230 away from the actuator 210. To reengage the sleeve 230 in a locked position, a user may rotate the sleeve 230 upwards to the locked position by turning the sleeve 230. In some embodiments, an audible noise—or click—may be heard when the sleeve 230 reengages with the collar 220 in a locked position. Such audible noise may be caused by a boss 222 on the sleeve 230 snapping over a retention lug 232 on the collar 220. The audible noise may inform a user that the sleeve 230 is again seated in a locked position.

According to some embodiments of the invention, a boss 222 may include a sloping surface 222s as illustrated in FIGS. 14 and 15. A sloping surface 222s may facilitate movement of a sleeve 230 from an open position to a closed or locked position. For example, a sleeve 230 positioned in an open position as illustrated in FIG. 22 may be rotated upward towards a locked position as illustrated in FIG. 21. As sleeve 230 is rotated and the one or more bosses 222 travel along a track 234, the upper or leading edge of the one or more bosses 222 engage one or more retention lugs 232 on the collar 220. The one or more retention lugs 232 may have a corresponding sloped surface 232s such that as the one or more bosses 222 engage with the one or more retention lugs 232, the boss 222 sloped surface 222s engages with the retention lug 232 sloped surface 232s to gradually deform the sleeve 230, allowing the one or more bosses 222 to pass over the one or more retention lugs 232 such that the sleeve 230 may be positioned in a locked position.

In some instances, it may be desirable to have a sleeve 230 and collar 220 combination that is "child-resistant," "senior friendly" or both "child-resistant" and "senior friendly." Such combinations may be utilized in those instances where a sprayer 200 is being utilized to store or deliver a drug or other material requiring special dosing considerations. Sprayers according to various embodiments of the invention may meet such criteria.

For example, according to some embodiments of the invention, a boss 222 on a sleeve 230 may include an engagement edge 222e having a negative angle. For example, the boss 222 illustrated in FIG. 15 may include a negative angle. As illustrated, the engagement edge 222e of the boss 222 is not normal to the interior surface of the sleeve 230; rather the engagement edge 222e is slightly angled relative to the interior surface normal at the point of contact between the interior surface of the sleeve 230 and the boss 222 engagement edge 222e. According to various embodiments of the invention, the engagement edge 222e may be between about 0.5 degrees and 2 degrees off normal. In other embodiments, engagement edge 222e may be between about 0.5 and 5 degrees off normal. In still other embodiments, the engagement edge 222e may be more than 0.5 degrees off normal relative to the interior surface of the sleeve 230.

During operation or movement of a sleeve 230 having a boss 222 with an engagement edge 222e having an angle off normal, the off normal angle helps bind the sleeve 230 to the collar 220—or boss 222 to the retention lug 232—while force is applied to the finger pads 236 in an attempt to disengage the sleeve 230 from the collar 220. This additional binding increases the deflection of the sleeve 230 required to disengage a boss 222 from an engagement tug 232. In some instances, the increased deflection required as a result of the off normal angle of the boss 222 engagement edge 222e improves the "child-resistant" qualities of the sleeve 230 and collar 220 engagement.

Figure 23:
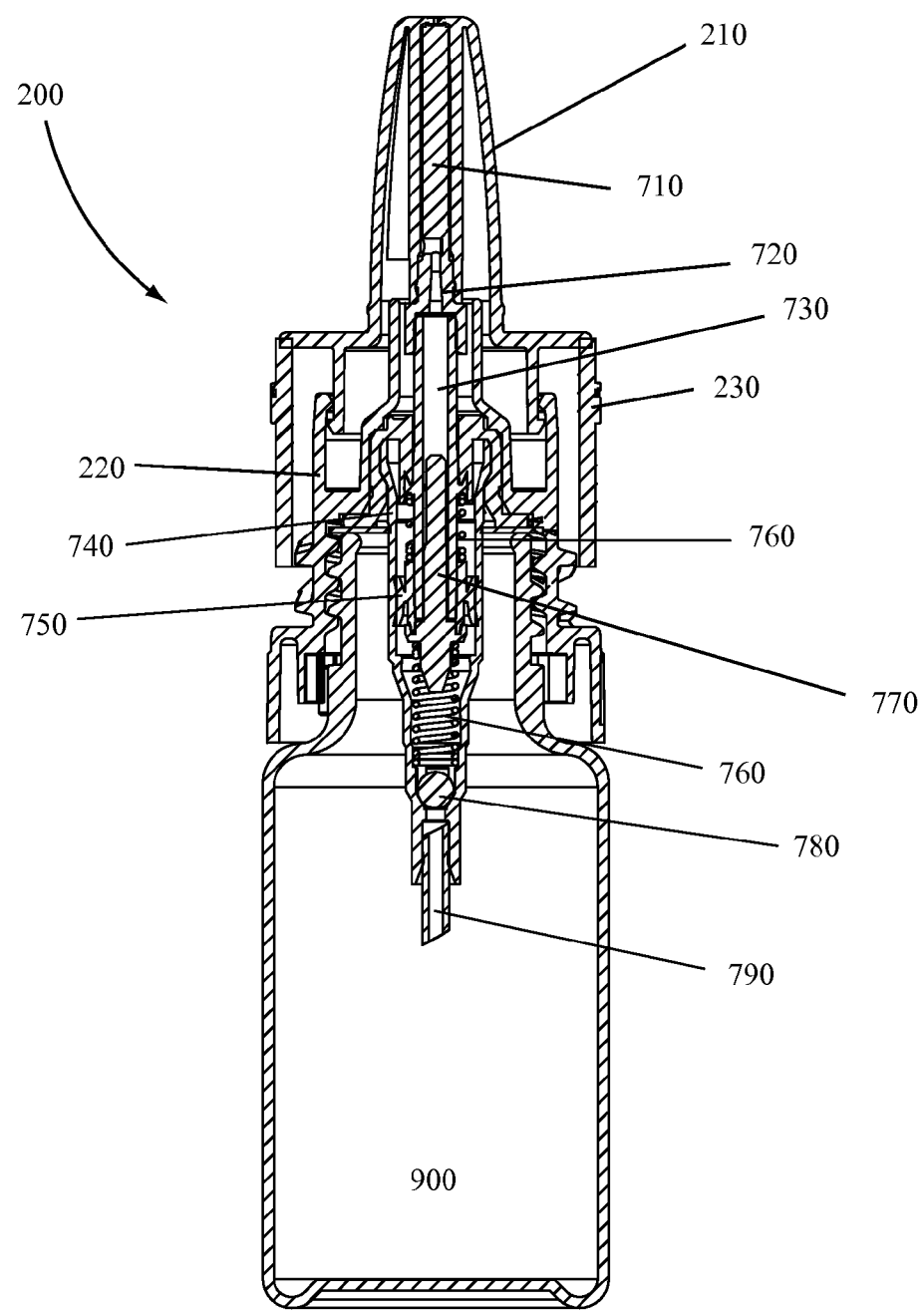
FIG. 23 illustrates a sprayer according to various embodiments of the invention.

FIG. 23 illustrates a sprayer 200 according to still other embodiments of the invention. As illustrated, the sprayer 200 may include a collar 220 attached to a bottle 900. A sleeve 230 may be moveable relative to the collar 220 such that sleeve 230 may prevent actuation of an actuator 210 in communication with the collar 220 in a first, locked position, and allow movement of the actuator 210 relative to the collar 220 in a second; unlocked position. The actuator 210 may be in communication with a pump or pump mechanism as known in the art. For example, as illustrated in FIG. 23, a pump mechanism may include an accumulator 740 seated in an opening of the container 900. A piston 750, valve 770; ball valve 780, springs 760 and piston stem 730 may be seated or arranged in the accumulator 740 forming a pump. A piston stem 730 may extend through the collar 220 into the actuation stop 281 but stop short thereof. The piston stem 730 may be in communication with a plug 720 and fluid flow insert 710 in the actuator which may direct the flow of fluid from the pump, through the actuator and out the sprayer 200. While a particular pump configuration is illustrated, it is understood that other configuration could also be include with various embodiments of the invention.

The components of sprayers according to various embodiments of the invention may be made from plastic, resin materials, metal, or other composites and materials as desired. While various embodiments of the invention have been described with respect to different sprayer configurations, it is understood that features from embodiments of sprayer 100 may be incorporated with embodiments of sprayer 200 and that features of the various embodiments of sprayer 200 may be incorporated with various embodiments of a sprayer 100.

Having thus described certain particular embodiments of the invention, it is understood that the invention defined by the appended claims is not to be limited by particular details set forth in the above description, as many apparent variations thereof are contemplated. Rather, the invention is limited only be the appended claims, which include within their scope all equivalent devices or methods which operate according to the principles of the invention as described.

What is claimed is:

1. A nasal sprayer, comprising:
   a container having a neck;
   a collar attached to the container neck, the collar further comprising:
      at least one boss on an outer surface of the collar; and
      at least one collar stop lug on an outer surface of the collar opposite the end nearest the container;
   a sleeve surrounding and engaged with the collar and moveable from a locked position to an unlocked position, the sleeve further comprising:
      at least one cam groove on an interior surface of the sleeve, wherein the at least one boss is seated in the at least one cam groove;
      at least one retention lug on a surface of the at least one cam groove, wherein the at least one retention lug engages the at least one boss of the collar in the locked position;
      at least one finger pad located on an exterior surface of the sleeve; and
      at least one stop lug on an interior surface of the sleeve;
   an actuator mounted to a pump and the container, wherein the actuator may be actuated when the sleeve is in the unlocked position.

2. The sprayer of claim 1, wherein the actuator comprises an actuator selected from the group consisting of a nasal actuator, a finger actuator, and a fine mist actuator.

3. The nasal sprayer of claim 1, wherein the sleeve further comprises a removable tear strip on a portion of the sleeve closest the container, wherein the tear strip must be removed before moving the sleeve from a locked to an unlocked position.

4. A sprayer, comprising:
   a container having a neck;
   a pump in communication with an interior of the container;
   an actuator mounted to the pump;
   a collar attached to the neck, the collar comprising:
      at least one track on an outer surface of the collar; and
      at least one retention lug positioned within a portion of the track; and
   a sleeve surrounding at least a portion of the collar, wherein the sleeve is moveable from a locked position to an unlocked position, the sleeve comprising at least one boss on an inner surface of the sleeve, wherein the at least one boss is positioned in the at least one track and engages the at least one retention lug in the locked position.

5. The sprayer of claim 4, wherein the at least one track comprises:
   a first track on the outer surface of the collar; and
   a second track on the outer surface of the collar, wherein the first track and second track are on opposite sides of the collar.

6. The sprayer of claim 4, wherein the at least one track further comprises:
   an upper guide rail; and
   a lower guide rail, wherein the upper guide rail and lower guide rail are spaced apart from one another and define the at least one track.

7. The sprayer of claim 4, wherein the at least one track further comprises an upper guide rail sloping upwards from a lower portion of the collar to a midpoint of the collar and then angling substantially vertically to an upper portion of the collar.

8. The sprayer of claim 7, wherein the sleeve further comprises at least one sleeve stop lug, the at least one sleeve stop lug in contact with a portion of the upper guide rail angling substantially vertically when the sleeve is in a locked position.

9. The sprayer of claim 4, wherein the collar further comprises at least one positive stop at a base of the at least one track.

10. The sprayer of claim 4, wherein the collar further comprises at least one pinch restrictor at a base of the at least one track.

11. The sprayer of claim 4, wherein the at least one boss further comprises:
   a positioning angle on the inner surface of the sleeve corresponding to an angle of the track; and
   a sloping surface.

12. The sprayer of claim 11, wherein the at least one retention lug further comprises a sloped surface.

13. The sprayer of claim 4, wherein the sleeve further comprises at least two finger pads on an exterior surface of the sleeve.

14. The sprayer of claim 13, wherein the at least two finger pads are on opposite sides of the sleeve.

15. The sprayer of claim 4, wherein the collar retains the pump on the container.

16. The sprayer of claim 4, wherein the pump is connected to the collar.

* * * * *